United States Patent [19]

Hardwicke, III

[11] Patent Number: 4,691,033

[45] Date of Patent: Sep. 1, 1987

[54] PROCESS FOR PREPARING 3-PHENOXYBENZALDEHYDES

[75] Inventor: James E. Hardwicke, III, Columbia, S.C.

[73] Assignee: Hardwicke Chemical Company, Elgin, S.C.

[21] Appl. No.: 811,403

[22] Filed: Dec. 20, 1985

[51] Int. Cl.$^4$ .......................................... C07D 317/34
[52] U.S. Cl. .................................................. 549/453
[58] Field of Search ........................................ 549/453

[56] References Cited

U.S. PATENT DOCUMENTS 3,997,567 12/1976 Kathawala ........................... 549/453
4,284,825 8/1981 Degner et al. ....................... 568/592

FOREIGN PATENT DOCUMENTS 1539733 1/1979 United Kingdom .
2055799 5/1983 United Kingdom .

*Primary Examiner*—Nicky Chan
*Attorney, Agent, or Firm*—Donald L. Johnson; John F. Sieberth; Patricia J. Hogan

[57] ABSTRACT

3-Phenoxybenzaldehyde acetals can be prepared by reacting a 3-bromobenzalkehyde acetal with an alkali metal phenolate at a temperature of about 130°–165° C. in the presence of a copper catalyst and a phenol as the sole solvent. The product acetals can be converted to the corresponding 3-phenoxybenzaldehydes by hydrolysis.

12 Claims, No Drawings

PROCESS FOR PREPARING 3-PHENOXYBENZALDEHYDES

FIELD OF INVENTION

This invention relates to 3-phenoxybenzaldehydes and more particularly to a process for preparing them.

BACKGROUND

As disclosed in British Pat. Nos. 1,539,733 (Sheldon et al.) and 2,055,799 (Thiault et al.), it is known that 3-phenoxybenzaldehydes are useful as pesticide intermediates and that they can be prepared from 3-bromobenzaldehyde acetals. Sheldon et al., who react their acetals with phenols or alkali metal phenolates in the presence of a copper catalyst, require an aprotic organic solvent for their reaction. Tiault et al. avoid the need for the aprotic solvent by reacting their acetal with an excess of phenol in the presence of a copper catalyst and potassium carbonate at a temperature of 170°-210° C.

Although the process of Thiault et al. is advantageous in that it avoids several problems associated with the use of the solvents of Sheldon et al., it also has its disadvantages. The elevated temperatures required for the reaction lead to degradation of the acetal, and the potassium carbonate appears to poison the catalyst. Thus, the obtainable yield of product is comparatively low.

SUMMARY OF INVENTION

An object of this invention is to provide a novel process for preparing 3-phenoxybenzaldehydes and acetal intermediates therefor.

Another object is to provide such a process that requires no aprotic organic solvent.

A further object is to provide such a process that can be conducted at moderate temperatures.

These and other objects are attained by reacting a 3-bromobenzaldehyde acetal with an alkali metal phenolate at a temperature of about 130°-165° C. in the presence of a copper catalyst and a phenol as the sole solvent to prepare a 3-phenoxybenzaldehyde acetal and, if desired, hydrolyzing the resultant acetal with an acid to form a 3-phenoxybenzaldehyde.

DETAILED DESCRIPTION

3-Bromobenzaldehyde acetals (bromoacetals) that can be used in the practice of the invention are the acetals derived from 3-bromobenzaldehydes and dihydric alcohols, such as ethylene glycol. The 3-bromobenzaldehyde may be substituted or unsubstituted, any substitutents being inert substitutents (i.e., substituents that will not prevent the reaction from occurring), such as alkyl, aryl, and alkoxy groups containing 1–10 carbons. A preferred 3-bromobenzaldehyde acetal is 3-bromobenzaldehyde acetal itself.

The alkali metal phenolate that is reacted with the bromoacetal is an alkali metal salt of phenol or a substituted phenol bearing one or more inert substituents, such as the optional substituents on the bromobenzaldehyde. The preferred phenolates are soduim and postassium phenolates, with the potassuim phenolates being particularly preferred in the interest of driving the reaction to completion. However, when it is desired to use a sodium salt, complete reaction can be achieved by employing it in conjunction with a small amount of potassium salt, e.g., about 10% of the total salt. The most prefered phenolates are generally the salts of phenol itself. The phenolate is preferably employed in excess, e.g., in a phenolate/bromoacetal mol ratio of at least about 1.1/1, optimally about 1.12/1, to drive the reaction to completion. Except for the practical limitations of economics and the size of the reaction vessel, there does not appear to be any maximum to the amount of phenolate that may be used.

The phenol employed as a solvent, like the phenolic moiety of the phenolate, may be a substituted or unsubstituted phenol, and it is most practically the phenol corresponding to the phenolic moiety of the phenolate. It is generally employed in a phenol/phenolate mol ratio of at least about 0.14/1, most commonly about 0.5/1. Higher mol ratios, e.g., about 1/1 are apt to be preferred as minimum mol ratios when the phenolate is a soduim salt; and even higher mol ratios can be employed if desired, regardless of the nature of the phenolate, since there does not appear to be any maximum to the amount of phenol that may be used. However, it is generally preferred to avoid using too large an excess of the phenol because of the larger reaction vessel that would be required to accomodate it.

The copper catalyst may be a cuprous or cupric compound, e.g., a chloride, bromide, iodide, fluoride, oxide, p-chlorobenzoate, phenolate, etc. However curpic or cuprous chloride is generally perferred. It is used in catalytic amounts, e.g., about 0.001–0.1 mol per mol of bromoacetal.

The reaction is conducted by mixing the bromoacetal, phenolate, phenol, and copper catalyst and heating the mixture at about 130°-165° C., preferably about 140°-150° C., to effect conversion of the bromoacetal to the corresponding phenoxyacetal, i.e., a 3-phenoxybenzaldehyde acetal. Temperatures substantially above 165° C. should be avoided because of increased tar formation as the temperature is increased, and temperatures below about 130° C. are undesirable becaus of the reduced reaction rate at lower temperatures. The time required for the reaction varies with factors like the particular temperature employed but is frequently in the range of about 2–4 hours.

In a preferred embodiment of the invention, the reaction is conducted as the final step of a total reaction that comprises (1) reacting the 3-bromoacetaldehyde with a dehydric alcohol by conventional means to prepare the bromoacetal, (2) separately reacting the phenol with an alkali metal hydroxide in amounts such as to provide the particular amounts of phenol and phenolate desired in the coupling reaction mixture, the reaction being conducted in a suitable solvent, such as xylene, at a suitable temperature, such as reflux temperature, and the water of reaction and the solvent being removed during the reaction and/or after the phenolate has been formed, and (3) adding the copper catalyst to the phenolate/phenol mixture formed in step 2, adding the bromoacetal formed in step 1 gradually or as a single charge, and heating the resultant mixture at about 130°-165° C.

After completion of the reaction, the phenoxyacetal may be converted to the corresponding 3-phenoxybenzaldehyde by conventional means. Typically, the phenoxyacetal is hydrolyzed with hydrochloric acid, although, as mentioned by Thiault et al., other strong acids are also utilizable.

The invention is particularly advantageous as a means of preparing 3-phenoxybenzaldehydes and their acetal intermediates under moderate conditions while avoiding the problems inherent in the use of aprotic organic solvents. The moderate temperatures permitted by the absence of potassium carbonate minimize tar formation and minimize reduction of the bromoacetal during the coupling reaction.

The following example is given to illustrate the invention and is not intended as a limitation thereof.

EXAMPLE

PART A

A suitable reaction vessel was charged with one molar porportion of 3-bromobenzaldehyde, 1.46 molar proportions of ethylene glycol, and 0.002 molar proportion of toluene/xylene sulfonic acid and warmed to 155° C. Water formed by the reaction was allowed to distill out and collect in a receiver. When the rate slowed, vacuum was applied to strip out the remaining water and the excess ethylene glycol. Conversion to 3-bromobenzaldehyde acetal was 98–99%.

PART B

A suitable reaction vessel was charged with 0.2 molar proportion of xylene, 1.82 molar porportions of phenol, and 1.12 molar proportions of KOH. The mixture was heated until about 1.5 molar proportions of water were collected. The potassium phenolate was cooled below reflux and one molar proportion of the 3-bromobenzaldehyde acetal of Part A was added. The temperature was adjusted to 130°–135° C. and the xylene solvent was stripped off under vacuum.

PART C

Nitrogen was applied to the reaction mixture of Part B to break the vacuum, and 0.002 molar proportion of cuprous chloride was added. The reaction was stirred for 3.5–4 hours at 130°–145° C. and cooled to 90° C. About 11 molar proportions of water were added, and the pH was adjusted to 6 with dilute HCl. GC analysis of the organic layer showed a 99% conversion of the statring bromoacetal with a 98% selectivity to 3-phenoxybenzaldehyde acetal.

PART D

KBr was drained off from the crude product of Part C, which was then heated under vacuum to strip out the excess phenol. The crude product was then hydrolyzed with about 0.06 molar proportion of HCl added as 2.5% HCl at 90°–100° C. for 30 minutes three times. The resulting 3-phenoxybenzaldehyde was then distilled at 140°–145° C. best vacuum. The yield, based on 3-bromobenzaldehyde, was about 85%.

It is obvious that many variations can be made in the products and processes set forth above without departing from the spirit and scope of this invention.

What is claimed is:

1. In a process for preparing a 3-phenoxybenzaldehyde acetal by reacting a 3-bromobenzaldehyde acetal with an alkali metal phenolate in the presence of a copper catalyst, the improvement which comprises conducting the reaction at a temperature of about 130°–165° C. in the presence of a phenol as the sole solvent.

2. The process of claim 1 wherein the acetal is 3-bromobenzaldehyde acetal.

3. The process of claim 1 wherein the alkali metal phenolate is sodium or potassium phenolate or a mixture thereof.

4. The process of claim 3 wherein the alkali metal phenolate is potassium phenolate.

5. The process of claim 3 wherein the alkali metal phenolate is a mixture of sodium phenolate and potassium phenolate.

6. The process of claim 1 wherein the copper catalyst is cuprous chloride.

7. The process of claim 1 wherein the copper catalyst is cupric chloride.

8. The process of claim 1 wherein the solvent is phenol.

9. The process of claim 1 wherein the phenolate/acetal mol ratio in the reaction mixture is at least about 1.1/1.

10. The process of claim 1 wherein the phenol/phenolate mol ratio in the reaction mixture is at least about 0.14/1.

11. The process of claim 10 wherein the phenol/phenolate mol ratio in the reaction mixture is at least about 0.5/1.

12. In a process for preparing a 3-phenoxybenzaldehyde by reacting a 3-bromobenzaldehyde acetal with an alkali metal phenolate in the presence of a copper catalyst and hydrolyzing the resultant 3-phenoxybenzaldehyde acetal, the improvement which comprises conducting the acetal-phenolate reaction at a temperature of about 130°–165° C. in the presence of a phenol as the sole solvent.

* * * * *